(12) United States Patent
Coronel

(10) Patent No.: US 10,391,005 B2
(45) Date of Patent: Aug. 27, 2019

(54) DIAPER ATTACHMENT SYSTEM

(71) Applicant: YKK CORPORATION OF AMERICA, Marietta, GA (US)

(72) Inventor: Wolfgang E. Coronel, Macon, GA (US)

(73) Assignee: YKK Corporation (JP)

( * ) Notice: Subject to any disclaimer, the term of this patent is extended or adjusted under 35 U.S.C. 154(b) by 990 days.

(21) Appl. No.: 14/865,386

(22) Filed: Sep. 25, 2015

(65) Prior Publication Data
US 2017/0087033 A1 Mar. 30, 2017

(51) Int. Cl.
A61F 13/56 (2006.01)
A61F 13/58 (2006.01)
A61F 13/62 (2006.01)

(52) U.S. Cl.
CPC ........ *A61F 13/565* (2013.01); *A61F 13/5622* (2013.01); *A61F 13/58* (2013.01); *A61F 13/62* (2013.01); *A61F 13/622* (2013.01); *A61F 2013/5694* (2013.01); *A61F 2013/587* (2013.01)

(58) Field of Classification Search
CPC ...... A61F 13/565; A61F 13/58; A61F 13/581; A61F 13/60; A61F 13/62; A61F 13/622; A61F 13/5622; A61F 2013/5694; A61F 2013/582; A61F 2013/583; A61F 2013/585; A61F 2013/586; A61F 2013/588; A61F 5/0104; A61F 5/0109; A61F 5/058; A61F 5/05858; A61F 5/05866; A44B 18/00
See application file for complete search history.

(56) References Cited

U.S. PATENT DOCUMENTS

| | | | |
|---|---|---|---|
| 4,002,172 A * | 1/1977 | Feldman | A61F 13/58 604/390 |
| 7,624,480 B2 | 12/2009 | Coronel | |
| 2002/0103470 A1 * | 8/2002 | Molander | A61F 13/49015 604/385.29 |
| 2009/0217492 A1 * | 9/2009 | Gallant | A44B 18/0003 24/306 |
| 2010/0004616 A1 * | 1/2010 | Nakamura | A61F 13/58 604/389 |
| 2011/0313389 A1 * | 12/2011 | Wood | A44B 18/0065 604/391 |

FOREIGN PATENT DOCUMENTS

JP 2010-110557 A 5/2010

OTHER PUBLICATIONS

International Search Report, PCT International Patent Application No. PCT/JP2016/07661, dated Dec. 13, 2016.
Written Opinion, PCT International Patent Application No. PCT/JP2016/07661, dated Dec. 13, 2016.

* cited by examiner

Primary Examiner — Tatyana Zalukaeva
Assistant Examiner — Gabriella E Burnette
(74) Attorney, Agent, or Firm — Kilpatrick Townsend & Stockton LLP

(57) ABSTRACT

Described is a diaper that includes an absorbent core and a chassis surrounding the absorbent core. The chassis may include a first end and a second end, the first end including at least two tabs. Each of the at least two tabs may include a fastening portion with a grip portion and a handle portion. Each grip portion is configured to removably attach to a portion of the second end, and each fastening portion may include at least one cut portion extending through an entire thickness of the fastening portion.

19 Claims, 9 Drawing Sheets

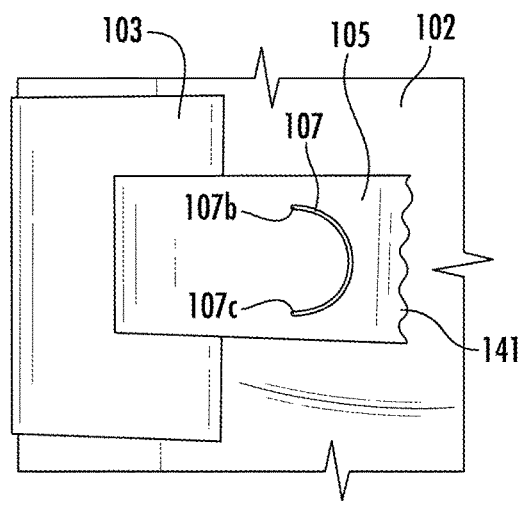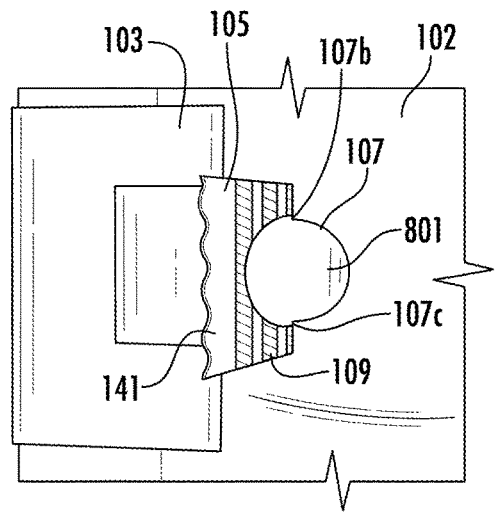
FIG. 7A   FIG. 7B
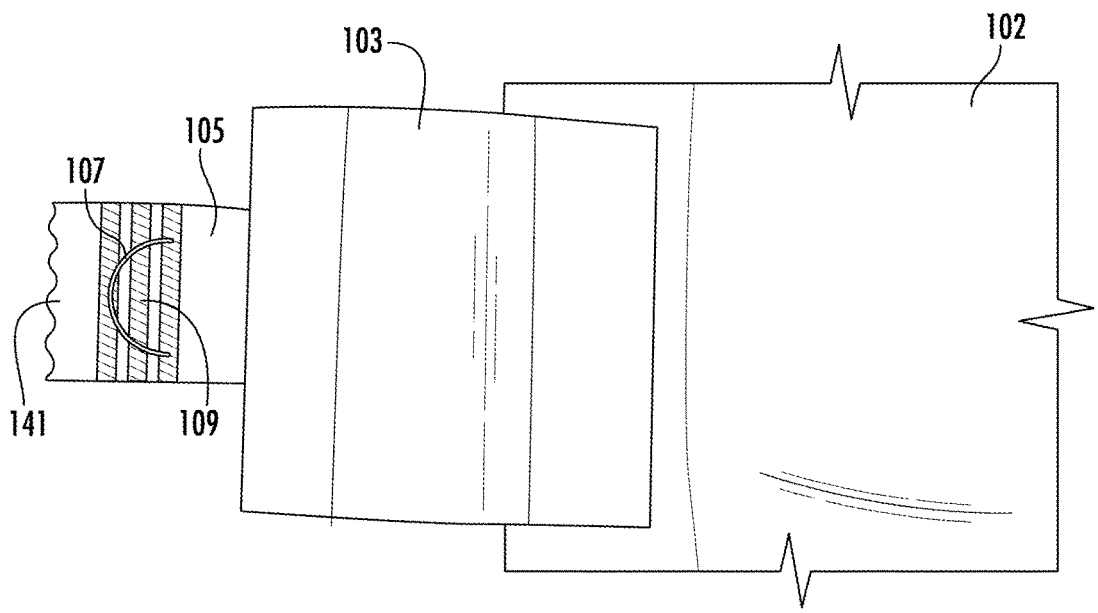
FIG. 7C

DIAPER ATTACHMENT SYSTEM

FIELD OF THE INVENTION

This invention relates to attachment devices for diapers and increasing the forces required for disengaging attachment devices for diapers or the like.

BACKGROUND

Diapers, for both children and adults, include attachment devices for securing the diaper in position. For example, diapers often include tabs that extend adjacent to or around a user's waist for attachment to another portion of the diaper. The design of the attachment device for some diapers may include inefficiencies or inadequate attachment strength that lead to unintended disengagement of the diaper.

In certain situations, it may be desirable to design diapers and related attachment devices to maximize strength and perceived strength when wearing and/or disengaging the diaper.

SUMMARY

The terms "invention," "the invention," "this invention" and "the present invention" used in this patent are intended to refer broadly to all of the subject matter of this patent and the patent claims below. Statements containing these terms should be understood not to limit the subject matter described herein or to limit the meaning or scope of the patent claims below. Versions of the invention covered by this patent are defined by the claims below, not this summary. This summary is a high-level overview of various aspects of the invention and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification of this patent, any or all drawings and each claim.

According to certain cases, a diaper comprises: an absorbent core and a chassis surrounding the absorbent core. The chassis includes a first end and a second end, the first end having at least two tabs and each of the at least two tabs having a fastening portion with a grip portion and a handle portion. Each of the grip portions is configured to removably attach to a portion of the second end and each fastening portion has at least one cut portion extending through an entire thickness of the fastening portion.

In some cases, at least one leading portion of the at least one cut portion, a first end point of the at least one cut portion, and a second end point of the at least one cut portion are disposed inside an area of the grip portion.

The at least one cut portion, in certain cases, has a concave shape where the at least one leading portion is disposed closer to the handle portion than the first and second end points.

In some cases, the at least one cut portion is a portion of a circular arc.

In certain cases, a width of the at least one cut portion is less than a minimum width of the handle portion.

The at least one cut portion, in certain cases, is four V-shaped cut portions.

In certain cases, the at least one cut portion includes at least one leading portion disposed within an area of the grip portion and two end points disposed outside the area of the grip portion.

In some cases, during disengagement of the fastening portion from the second end, the diaper is configured such that a peeling force resists detachment of the fastening portion from the second end before detachment of the fastening portion reaches a pair of end points of the at least one cut portion. Moreover, during disengagement of the fastening portion from the second end, the diaper is configured such that a shear force resists detachment of the fastening portion from the second end after detachment of the fastening portion reaches the pair of end points of the at least one cut portion.

In certain cases, the peeling force is applied to pull a portion of the grip portion outside of the at least one cut portion away from the second end of the diaper. In some cases, the shear force to applied to pull a portion of the grip portion inside of the at least one cut portion away from the second end of the diaper.

After pulling an area inside the at least one cut portion away from the second end of the diaper, in certain cases, the diaper is configured such that a second peeling force resists detachment of the fastening portion from the second end.

Also disclosed is an attachment tab for use with a diaper. The attachment tab includes a fastening portion with a handle portion disposed at a distal edge of the fastening portion and a grip portion. In some cases, the grip portion is disposed between the handle portion and an attachment between the fastening portion and the attachment tab and the grip portion is configured to removably attach to a second end of the diaper. Moreover, the fastening portion has at least one cut portion extending through an entire thickness of the fastening portion.

In some cases, a width of the at least one cut portion is less than a minimum width of the fastening portion.

The handle portion and the grip portion, in certain cases, each extend across a full width of the fastening portion.

In some cases, the at least one cut portion has at least one leading portion, a first end point, and a second end point.

The first end point and the second end point of the at least one cut portion, in certain cases, are disposed inside the grip portion.

In certain cases, the at least one cut portion has a concave shape where the at least one leading portion is disposed closer to the handle portion than the first and second end points.

In some cases, the at least one cut portion is a portion of a circular arc.

The grip portion, in certain cases, includes at least one of (i) adhesive, (ii) a plurality of hooks or (iii) a plurality of loops.

The attachment tab, in certain cases, further includes a second at least one cut portion disposed in the attachment tab adjacent to the attachment between the fastening portion and the attachment tab, as well as a second grip portion on the second end of the diaper configured to interface with the second at least one cut portion.

BRIEF DESCRIPTION OF THE DRAWINGS

Illustrative embodiments of the present disclosure are described in detail below with reference to the following drawing figures:

FIGS. 7A, 7B, and 7C illustrate the disengagement of an attachment system of the diaper of FIGS. 1A and 1B.

DETAILED DESCRIPTION

The subject matter of versions of the present invention is described here with specificity to meet statutory requirements, but this description is not necessarily intended to limit the scope of the claims. The claimed subject matter may be embodied in other ways, may include different elements or steps, and may be used in conjunction with other existing or future technologies. This description should not be interpreted as implying any particular order or arrangement among or between various steps or elements except when the order of individual steps or arrangement of elements is explicitly described.

Figure 1A:
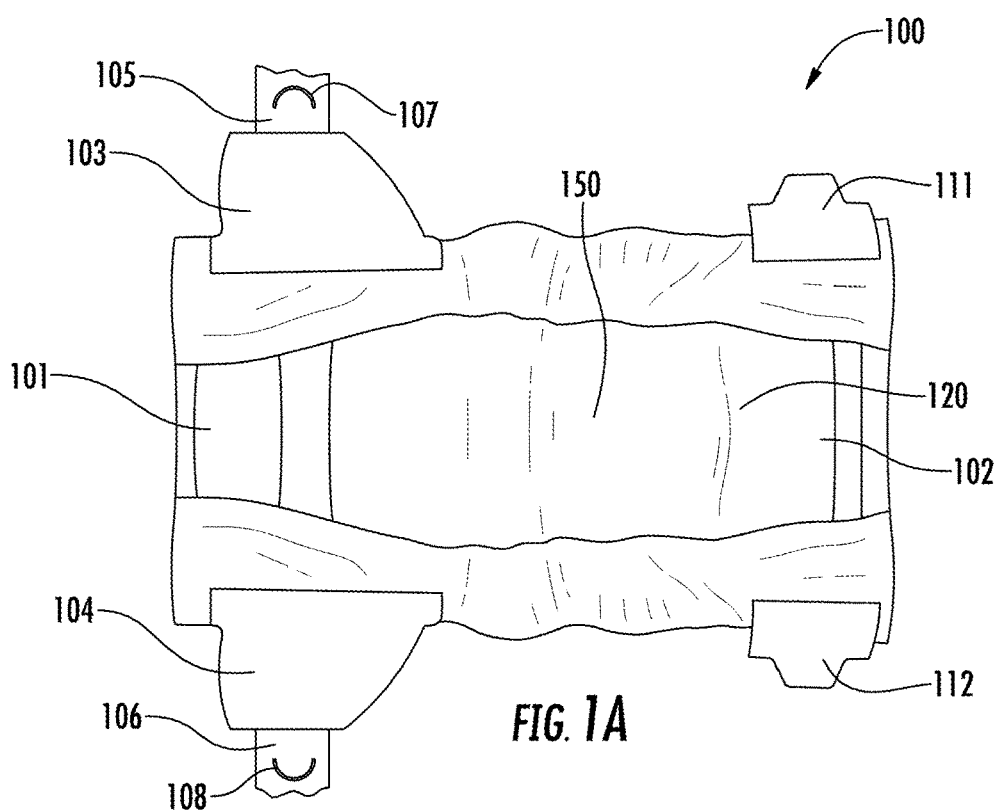
FIG. 1A is a top view of a diaper according to certain aspects.
Figure 1B:
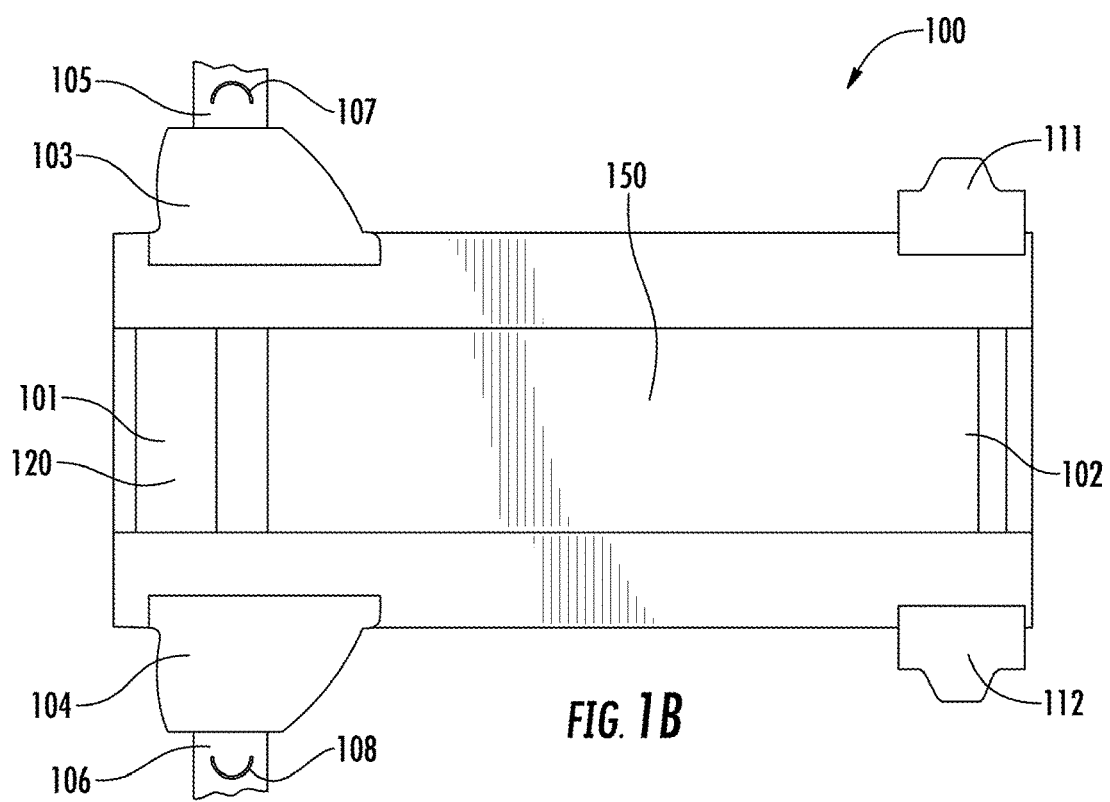
FIG. 1B is a top view of the diaper of FIG. 1A with the elastic members stretched.
Figure 2:
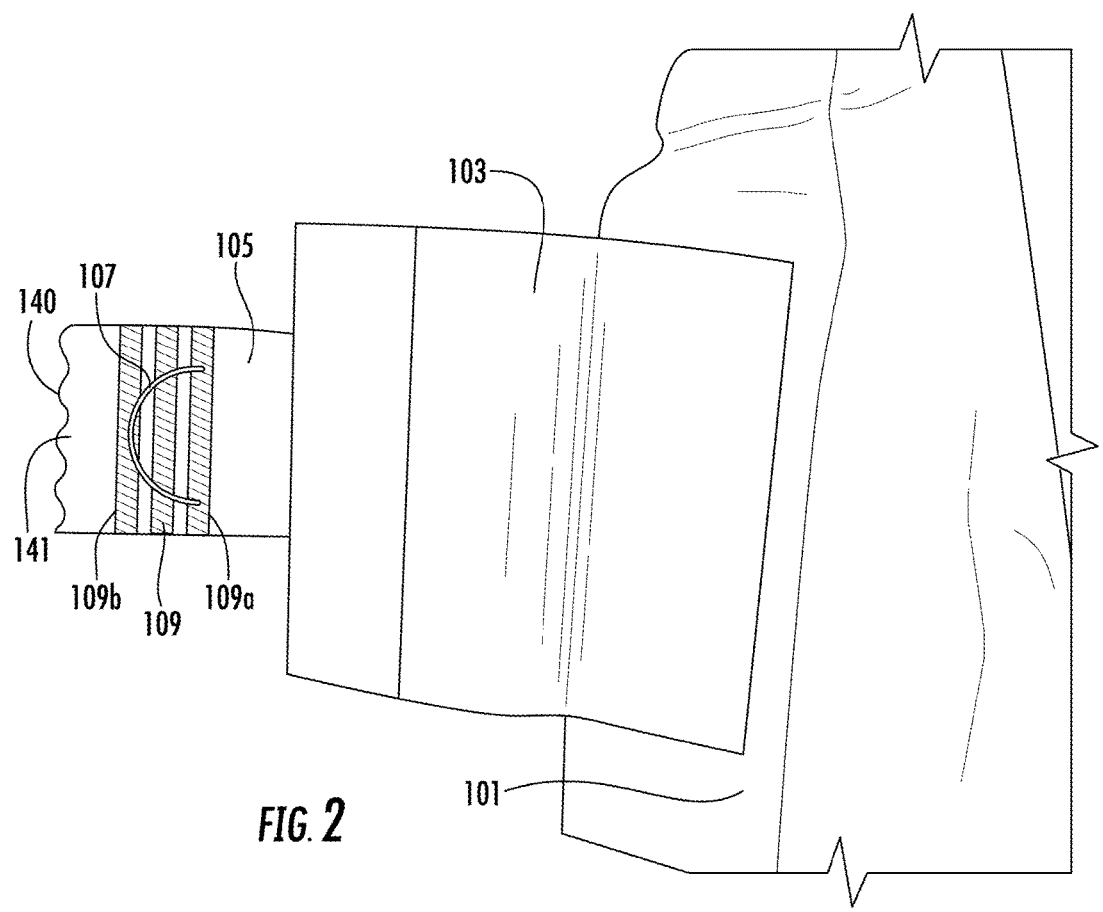
FIG. 2 is a detail view of a portion of the diaper of FIGS. 1A and 1B.
Figure 8A:
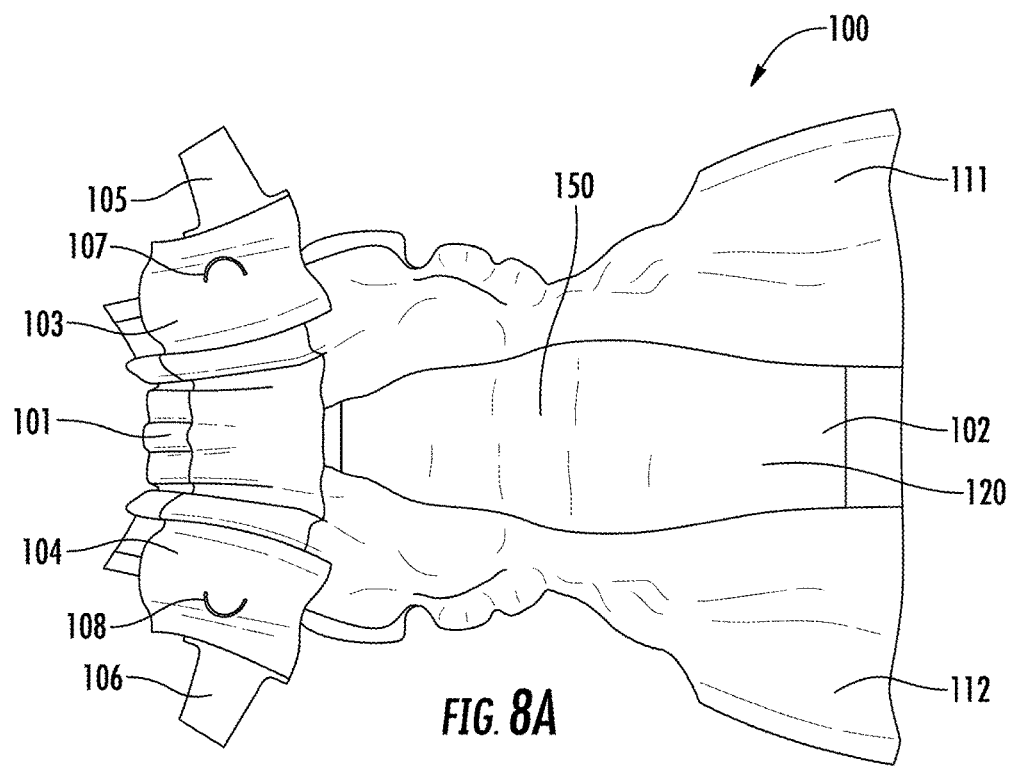
FIG. 8A is a top view of a diaper according to another aspect.
Figure 8B:
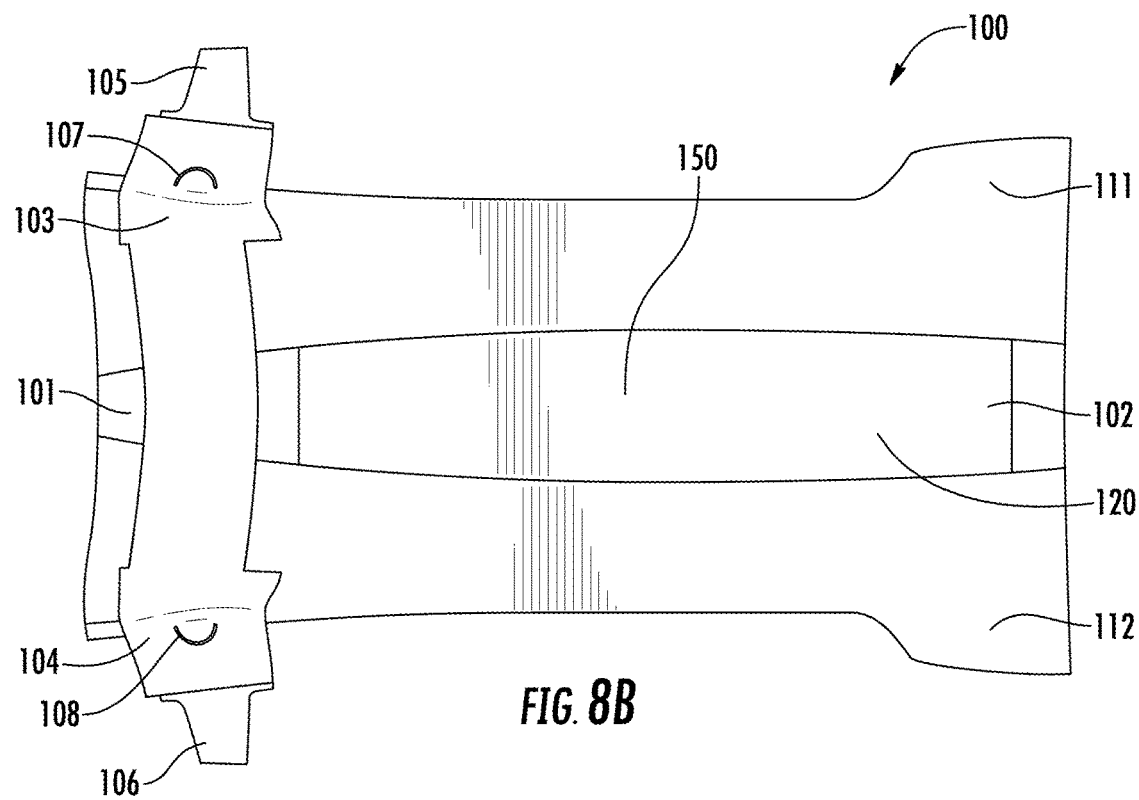
FIG. 8B is a top view of the diaper of FIG. 8A with the elastic members stretched.

FIGS. 1A and 1B depict a non-limiting diaper 100 and FIGS. 8A and 8B show another example of a diaper 100. For example, the diaper in FIGS. 8A and 8B shows tapered fastening portions and an elastic waistband aligned with the first end of the chassis 120. Although some of the same reference numbers are used for both the diaper of FIGS. 1A and 1B and the diaper of FIGS. 8A and 8B, the two sets of Figures are not meant to depict the same diaper. Furthermore, in some cases, individual features from the two diapers may be combined and/or substituted.

FIGS. 1A-9 illustrate versions of diapers 100 with improved attachment systems. In these cases, the diaper 100 may include a centrally located absorbent core 150, a chassis 120, and elastic surrounding the chassis. For example, as shown in FIGS. 1A and 1B, the diaper 100 may include a chassis 120 with a first end 101 and a second end 102. In certain cases, the diaper 100 may include one or more tabs attached to each end of the chassis 120. For example, as shown in FIGS. 1A and 1B, the diaper 100 may include a first attachment tab 103 and a second attachment tab 104 disposed adjacent to the first end 101 of the chassis 120. In some cases, one or both the first and second attachment tabs 103 and 104 may be integral to the outer layer(s) of the chassis 120 while, in other cases, the tabs may be separate components that are attached to the chassis 120. The diaper 100 may also include a third attachment tab 111 and a fourth attachment tab 112 disposed at the second end 102 of the chassis 120.

To secure the diaper 100 in a worn position, the diaper 100 may include an attachment system as described in more detail below. For certain cases of diaper 100, the worn position includes a configuration where the first end 101 is adjacent to a user's rear waste line (near the user's lower back), the second end 102 is adjacent to a user's front waste line (near the user's lower abdomen), and attachment tabs 103, 104 extend around the user's waist toward the second end 102.

In some cases, the attachment system may include one or more fastening portions that are used to secure one portion of the diaper to another portion of the diaper. The fastening portions may be a portion or area of one or more of the attachment tabs 103, 104, 111, 112 or may be a separate component attached to the respective tab. Any or all of the attachment tabs 103, 104, 111, 112 may include a fastening portion. As shown in FIGS. 1A and 1B, in some cases, the first attachment tab 103 includes a first fastening portion 105 and the second attachment tab 104 includes a second fastening portion 106.

As shown in FIGS. 2-6 (illustrating various versions of fastening portions), each fastening portion (e.g., first fastening portion 105 or second fastening portion 106) may include a handle portion 141 and a grip portion 109. The handle portion 141 may facilitate grasping or handling of the fastening portion. The grip portion 109 is configured to removably attach to another portion of the diaper. The grip portions 109 may be configured for adhesive fastening, hook and loop fastening, other types of fastening, or combinations thereof. The grip portion 109 may include (i) adhesive for an attachment, (ii) hooks for a hook and loop attachment, (iii) loops for a hook and loop attachment, or (iv) a combination of two or more of the preceding features.

Figure 3A:
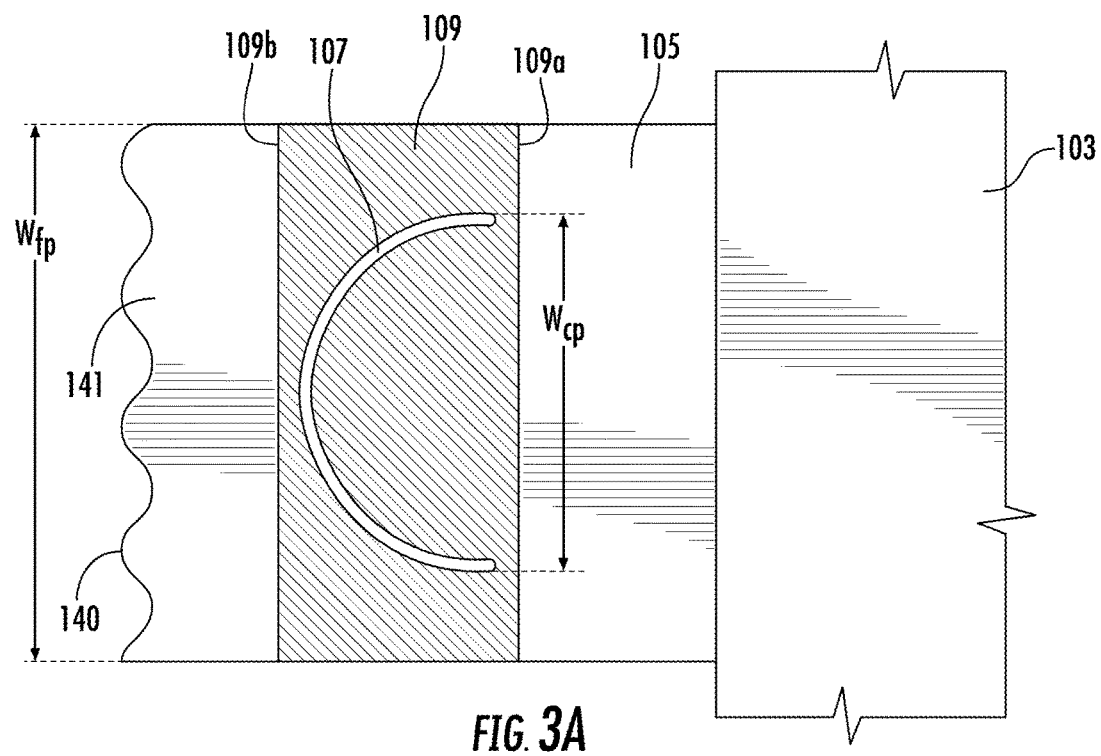
FIGS. 3A and 3B are detail views of alternate fastening portions that could be used with the diaper of FIGS. 1A and 1B.
Figure 3B:
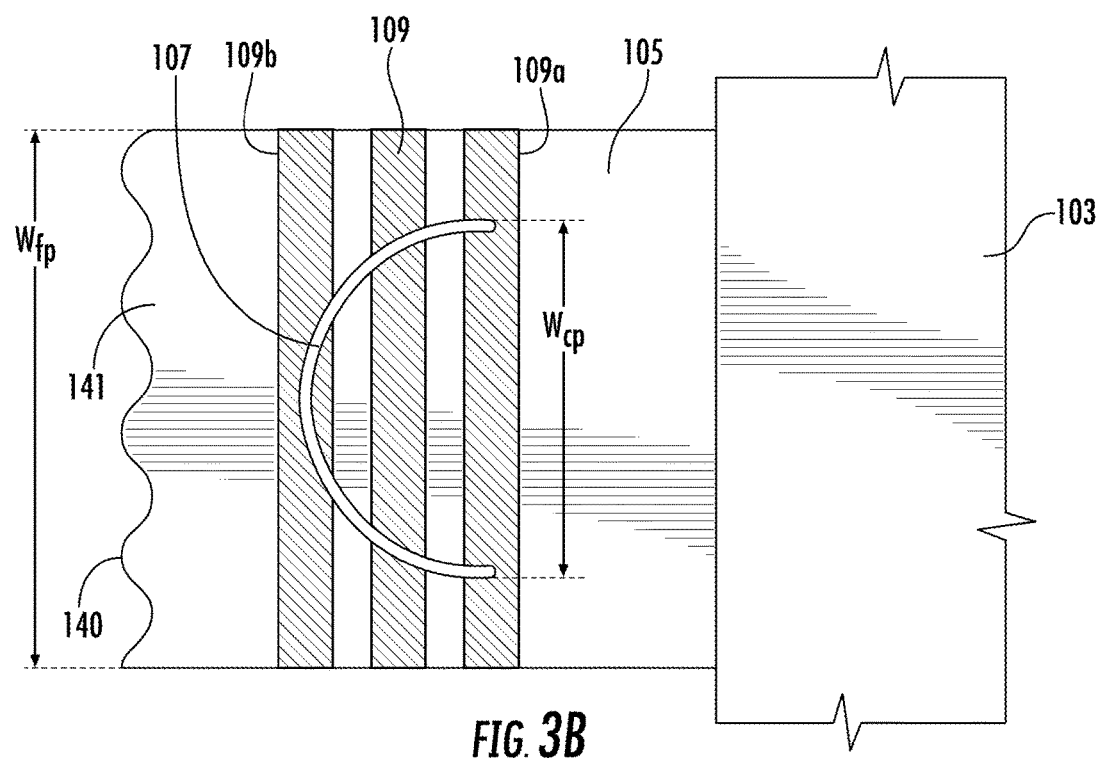

In some cases, the handle portion 141 is disposed adjacent to a distal edge 140 of the fastening portion. The fastening portion may also include a proximal edge opposite of distal edge 140. The grip portion 109 may cover the entire surface of the fastening portion or be confined a particular area of the fastening portion (e.g., the continuous rectangular area shown in FIG. 3A). The grip portion 109 may include a single continuous area, such as the rectangular grip portion 109, as shown in FIG. 3A, may include multiple distinct areas such as three rectangular strips adjacent one another as shown in FIG. 3B, or may be any other shape or area of the fastening portion.

As illustrated in the Figures, grip portion 109 may include a first edge 109a and a second edge 109b, where the second edge 109b is located closer to the handle portion 141 and the distal edge 140 of the fastening portion 105 than the first edge 109a. In certain cases, the grip portions 109 are configured to engage the second end 102 of the diaper 100. The second end 102 may have a specific grip portion (see grip portion 209 in FIG. 9) that engages the grip portions 109. In other cases, the grip portions of the first end 101 may interface with any portion of the second end 102.

The diaper attachment systems described herein typically have greater shear strength compared to peel strength for adhesive fastening, hook and loop fastening, other types of fastening, and combinations thereof. In other words, the force required to disengage the fastening portion 105 or 106 of diaper 100 from the surface of second end 102 with which it is engaged is greater than the force required for a conventional diaper, which relies solely on peeling forces. As described in greater detail below, disengagement for fastening portion 105 or 106 transitions between one or more peeling stages and one or more shear stages. In one example of a shear stage, the fastening portion 105 or 106 is pulled along the surface of second end 102 (i.e., moving the two surfaces in opposite directions along approximately parallel planes creating a shear force). In some cases, for hook and loop fasteners, the shear strength is approximately 24 times greater than the peel force for a given area.

To create the effect of greater strength for disengaging the attachment system of diaper 100 and to create an effect of a stepped or tiered magnitude for the magnitude of force required to disengage the attachment system of diaper 100, the fastening portion 105 may include one or more cut portions 107 and the fastening portion 106 may include one or more cut portions 108. In some cases, the one or more cut portions 107 extends through the entire thickness of the fastening portion 105.

Figure 4A:
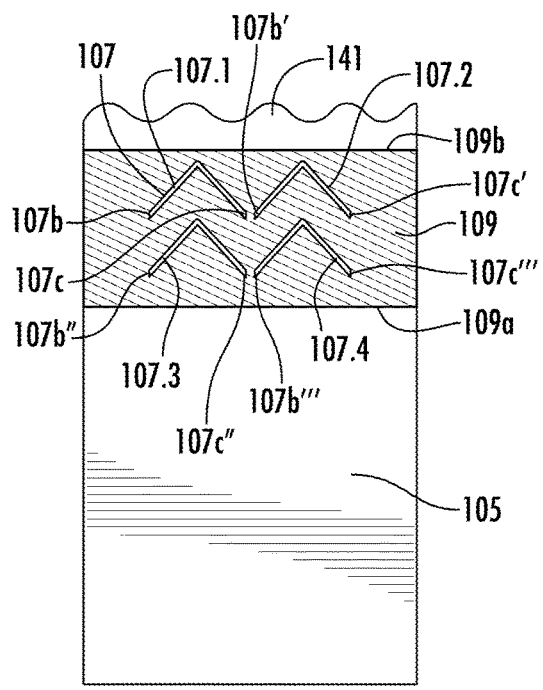
FIGS. 4A, 4B, 4C, and 4D are detail views of alternate fastening portions that may be used with the diaper of FIGS. 1A and 1B.
Figure 4B:
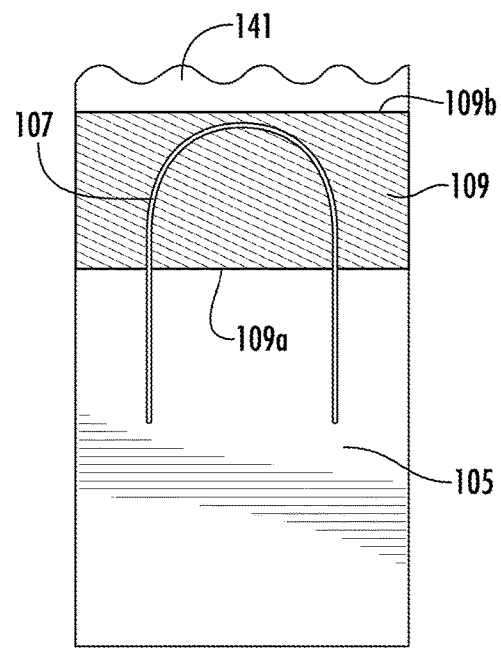
Figure 4C:
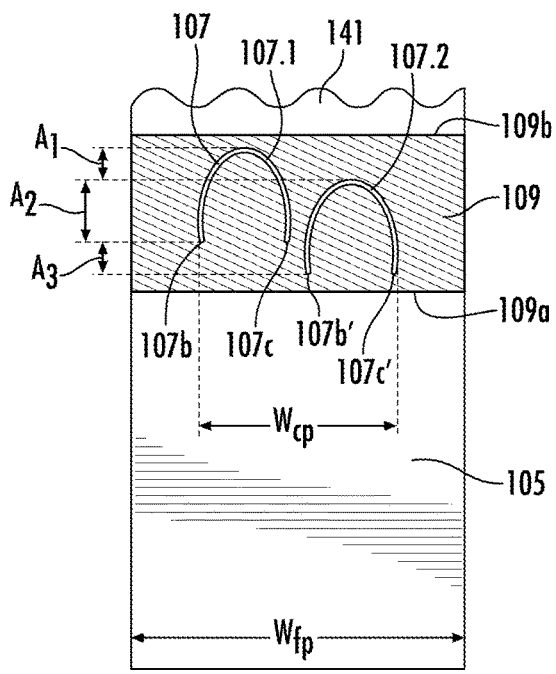
Figure 4D:
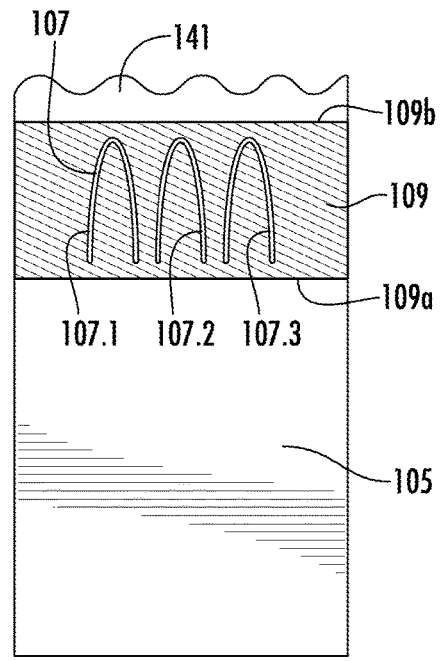
Figure 5:
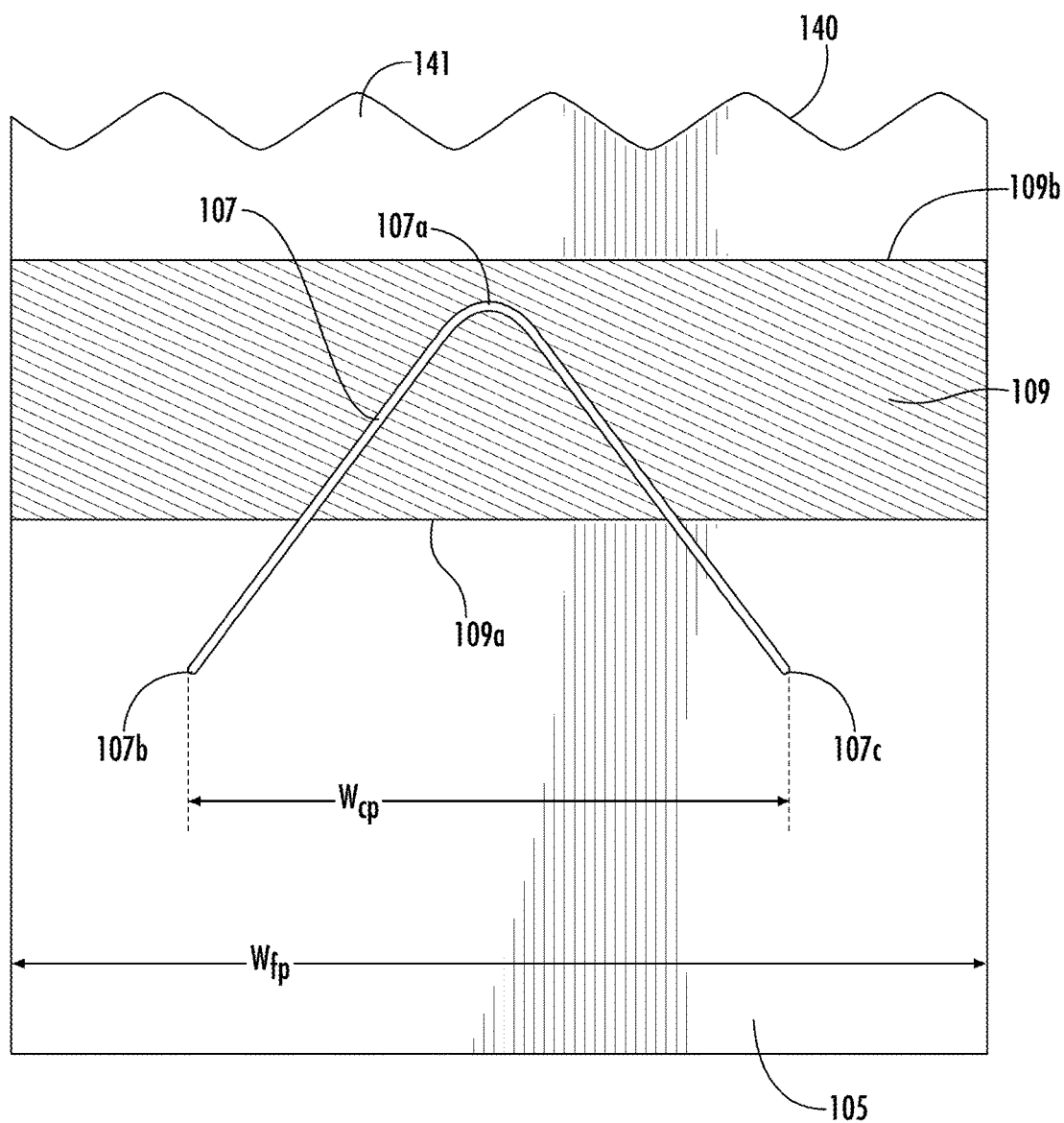
FIG. 5 is a detail view of another alternate fastening portion that may be used with the diaper of FIG. 1A-1B.
Figure 6:
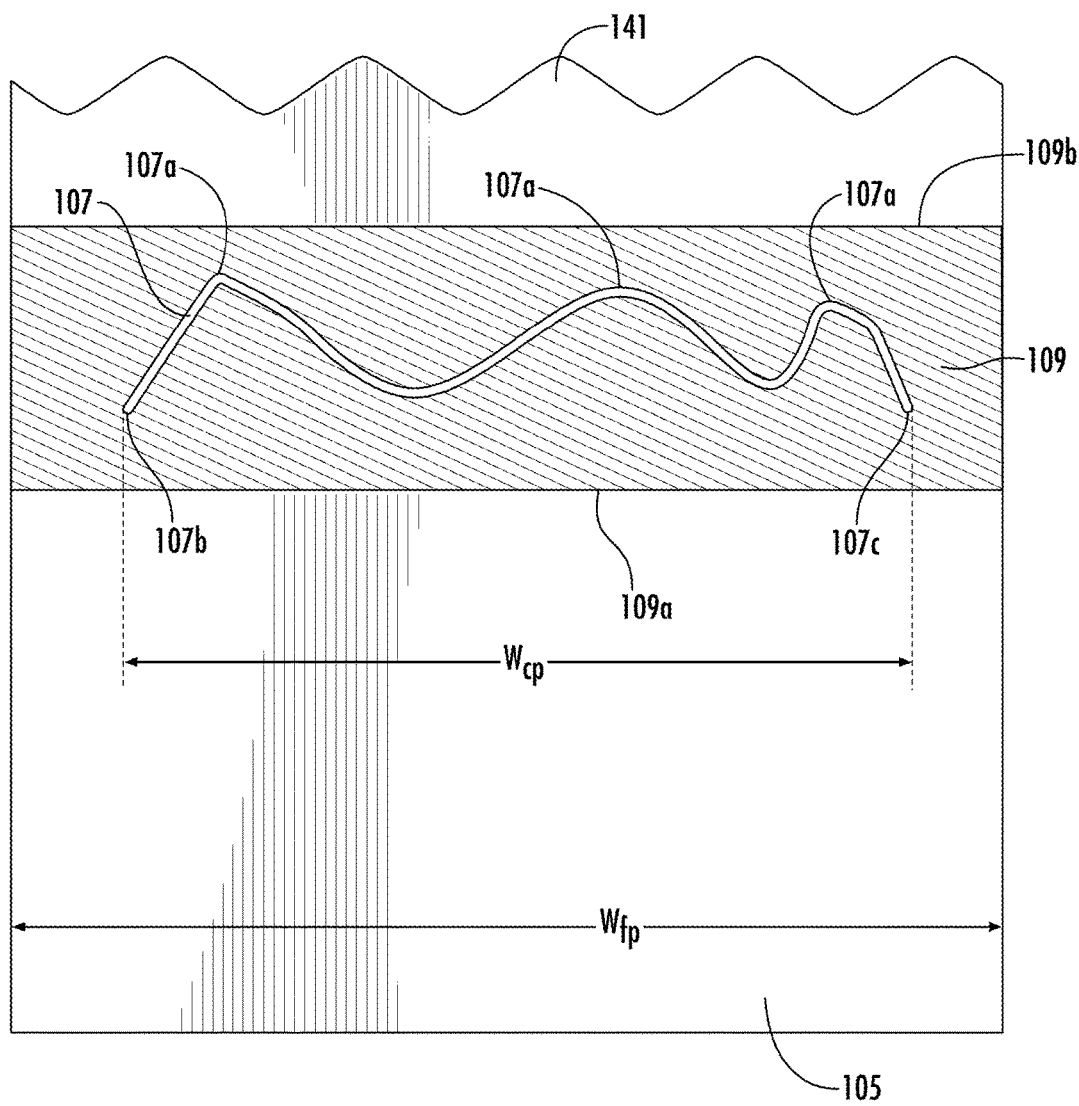
FIG. 6 is a detail view of another alternate fastening portion that may be used with the diaper of FIGS. 1A and 1B.

As shown in FIGS. 2-6, the cut portion 107 may comprise any suitable shape. In one non-limiting example, the cut portion 107 comprises a concave shape pointed away from the handle portion 141 and the distal edge 140 of the fastening portion 105. The shape of the area within the concave shape may be rounded or angular, or combinations thereof. As shown in FIGS. 5 and 6, the cut portion 107 may include one or more leading portions 107a (which may be a point or a segment of the cut portion 107) located closest (or closer than adjacent portions of cut portion 107) to the distal edge 140 of the fastening portion 105. The cut portion 107 may also include end points 107b and 107c. The leading portion 107a for the circular arc cut portion 107 shown in FIGS. 3A and 3B is the approximate middle of the circular arc adjacent to the handle portion 141 of the fastening portion 105. As shown in FIGS. 3A-6, the cut portion 107 may be a single cut (FIGS. 3A, 3B, 4B, 5, and 6) or may be multiple cuts (FIGS. 4A, 4C, and 4D) and, in some cases, may be an irregular and/or asymmetric shape (FIG. 6).

In some cases, as illustrated in FIGS. 3A, 3B, and 4C, all regions of the fastening portion 105 have an overall width (or a minimum width) of $W_{fp}$ that is greater than the width $W_{cp}$ of the cut portion 107. For example, the handle portion 141 and the grip portion 109 are each wider than the cut portion 107. The width of the handle portion 141 ($W_{fp}$) ensures sufficient resistance during peeling operations and provides adequate area for a user to grasp the fastening portion 105.

FIGS. 7A-7C illustrate the disengagement of the fastening portion 105 from the second end 102 of the diaper 100. The fastening portion 105 is shown fully engaged in FIG. 7A. To disengage the fastening portion 105 from the second end 102 of the diaper 100, the user begins by pulling the handle portion 141 away from the surface of second end 102. When a peeling force $F_p$ is applied to the handle portion 141, the concave shape of cut portion 107 causes the part of fastening portion 105 outside of cut portion 107 to peel away from the second end 102 of the diaper 100 while leaving the area 801 of the fastening portion inside the cut portion 107 still attached to the second end 102 (see FIG. 7B). The peeling force $F_p$ is applied away from the surface of second end 102 with a bias toward the first end 101 of the diaper 100. The bias toward the first end 101 of the diaper 100 occurs for two reasons: (1) the fabric of diaper 100 attached to the fastening portion 105 lifts when the fastening portion 105 is lifted (particularly the portions of diaper 100 closer to first end 101); and (2) fastening portion 105 pivots about its attachment to first attachment tab 103. The disengagement of the fastening portion 105 from the second end 102 of the diaper 100 occurs when the peeling force $F_p$ reaches the end points 107b and 107c as shown in FIG. 7B.

When the fastening portion 105 is pulled away to reach the end points 107b and 107c, the fastening portion 105 distributes load into the area 801 inside the cut portion 107, which is an approximate semicircular shape in FIG. 7B. Because the handle portion 141 of fastening portion 105 (where the disengagement load is applied) pulls from the left side of FIG. 7B (and not from the edge defined by cut portion 107), a shear force $F_s$ must be applied to remove the area 801 inside the cut portion in FIG. 7B. In other words, to complete the disengagement process and move beyond the state illustrated in FIG. 7B, a shear force $F_s$ must be applied, where the shear force $F_s$ is greater than the peeling force $F_p$. In some cases, the shear force $F_s$ is approximately 24 times greater than the peeling force $F_p$ for a given area. Thus, the disengagement process includes an initial stage where a peeling force $F_p$ is applied (between FIG. 7A and FIG. 7B) and a subsequent stage where a shear force $F_s$ is applied (between FIG. 7B and FIG. 7C).

The end points 107b and 107c of the cut portion 107 define a transition between the initial stage where the peeling force $F_p$ is applied and the subsequent stage where the shear force $F_s$ is applied. The end points 107b and 107c may be located inside the area of the grip portion 109 (see FIGS. 2-4A, 4C, 4D, and 6) or the end points 107b and 107c may be located outside the area of the grip portion 109 (see FIGS. 4B and 5). In some cases, where the end points 107b and 107c are located inside the grip portion 109, there may be a portion of the grip portion 109 (e.g., the far left and far right sides outside of the cut portions in FIGS. 4A, 4C, 4D, and 6) that requires a peeling force $F_p$ during the shear stage in addition to the shear force $F_s$.

In some cases, the disengagement process may include second or subsequent peeling stages (or a second peeling force $F_p$) applied after area 801 is removed from the second end 102. For example, the configuration illustrated in FIG. 4A may include a first peeling stage where a peeling force $F_p$ is applied (beginning at second edge 109b of grip portion 109) until the peeling process reaches the end points 107b, 107c, 107b', and 107c' of the upper two triangular cut portions 107.1 and 107.2. After reaching end points 107b, 107c, 107b', and 107c' of cut portions 107.1 and 107.2, a first shear stage begins where a shear force $F_s$ is applied to disengage the areas within cut portions 107.1 and 107.2. After the first shear stage is complete, a second peeling stage progresses until the peeling process reaches end points 107b''', 107c''', 107b''', and 107c''' of cut portions 107.3 and 107.4. After reaching the end points 107b''', 107c''', 107b''', and 107c''' of cut portions 107.3 and 107.4, a second shear stage begins where a shear force $F_s$ is applied to disengage the areas within cut portions 107.3 and 107.4. After the second shear stage is complete, a third peeling stage progresses until the peeling process reaches the first edge 109a of grip portion 109.

FIG. 4C shows another configuration where after the first peeling stage is complete, a first shear stage is based on an upper region of cut portion 107.1 (see $A_1$). A second shear stage occurs where the two cut portions 107.1 and 107.2 overlap (see $A_2$). The third shear stage corresponds to the lower region of the second cut portion 107.2 (see $A_3$).

Figure 9:
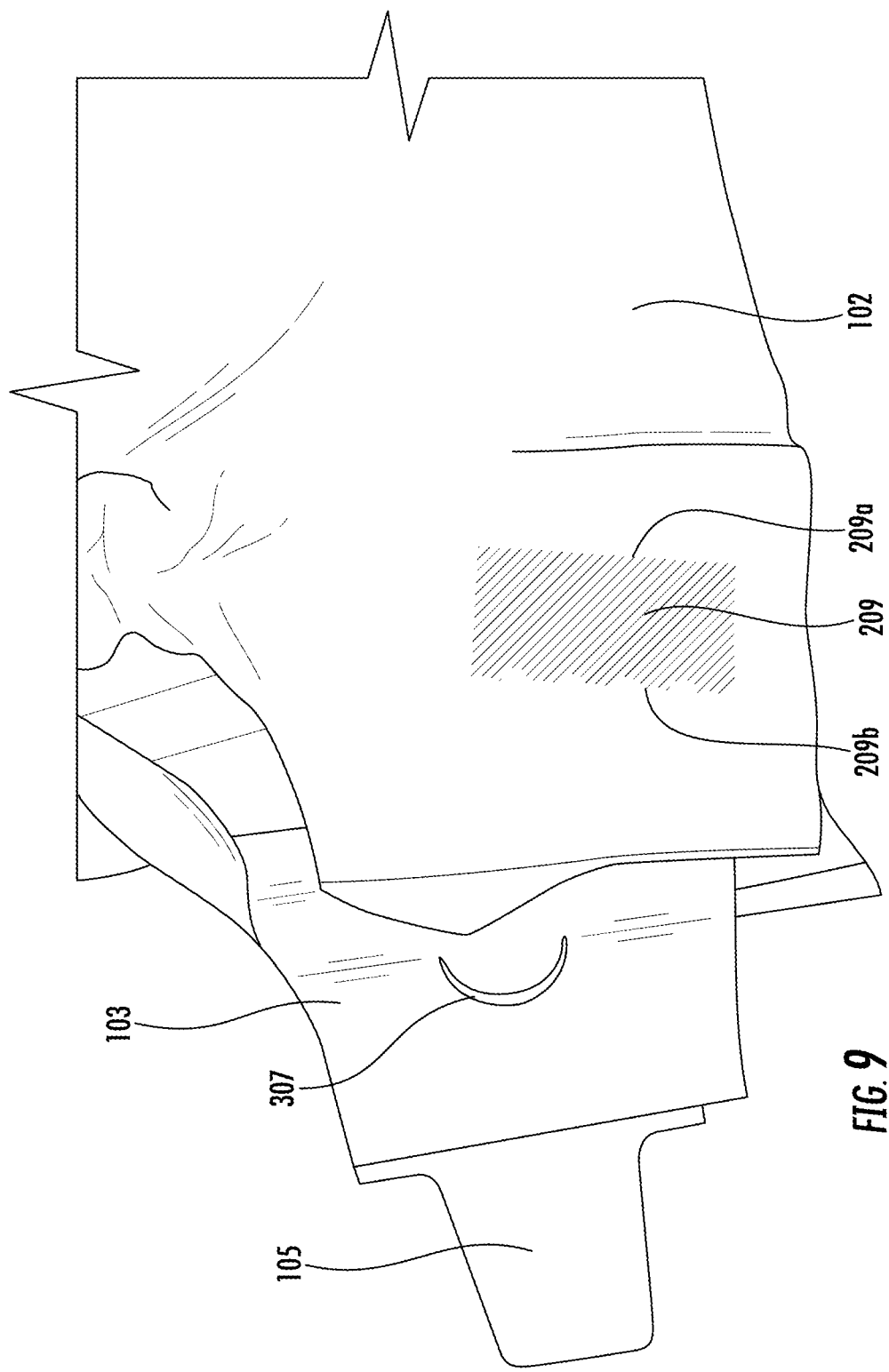
FIG. 9 is a top view of an attachment system of the diaper of FIGS. 8A and 8B.

In addition to or lieu of the rectangular shaped fastening portions shown in FIGS. 1A-7C, as illustrated in FIGS. 8A-9, the diaper 100 may include fastening portions 105 and 106 with a trapezoidal shape. In particular, the fastening portion 105 shown in FIG. 9 has a tapering width. The fastening portions may be any appropriate geometric shape such as but not limited to a square, rectangle, trapezoid, any other quadrilateral, pentagon, hexagon, heptagon, octagon, circle, or semicircle.

As described above, the grip portion 109 may be configured to interface with a specific region of the second end 102 or may be configured to interface with any surface of second end 102. For example, if grip portion 109 is configured to be an area with adhesive, grip portion 109 may (1) interface with a specific area of second end 102 (e.g., grip portion 209) that is configured to enhance the effect of the adhesive or (2) interface with any portion of the surface of second end 102. As shown in FIG. 9, the second end 102 may include a grip portion 209. The grip portion 209 may be configured to interface with fastening portion 105 (which may or may not include a grip portion 109). The grip portion 209 may comprise (i) adhesive for an attachment, (ii) hooks for a hook and loop attachment, (iii) loops for a hook and loop attachment, or (iv) a combination of two or more of the preceding features.

In some cases, the grip portion 209 may be configured to interface with a portion of first attachment tab 103. As shown in FIG. 9, the first attachment tab 103 may include one or more cut portions 307 such that the disengagement process when removing first attachment tab 103 from second end 102 includes an initial stage (peeling force $F_p$) and at least one subsequent stage (shear force $F_s$) similar to the disengagement of grip portion 109 described above. If desired, fastening portion 105 may also include one or more cut portions as described above.

In one example, grip portion 109 may include hooks for hook and loop attachment and the second end 102 may include loops for interfacing with the hooks of grip portion 109. The loops of second end 102 may be in a designated area (i.e., grip portion 209) or may cover any portion of second end 102. In another example, grip portion 109 may include loops for hook and loop attachment and the second end 102 may include hooks for interfacing with the loops of grip portion 109. The hooks of second end 102 (i.e., grip portion 209) may be configured to interface with a designated area of fastening portion 105 (i.e., grip portion 109) or may be configured to interface with any portion of fastening portion 105. In addition, in some cases, the diaper 100 may include both (1) a first attachment between fastening portion 105 and second end 102 as described above and (2) a second attachment between first attachment tab 103 and second end 102 as shown in FIG. 9. For the first and/or second attachment, the second end 102 may include one or more grip portions 209 (see FIG. 9). Furthermore, the first attachment may include a cut portion (e.g., cut portion 107 described above) and/or the second attachment may include a cut portion (e.g., cut portion 307).

The components of the diaper 100 may be formed of materials including, but not limited to, non-woven polypropylene, other non-woven materials, woven materials, other plastic materials, thermoplastic, metallic materials, other composite materials, cotton, wool, synthetic fabric, or other similar materials. Moreover, the components of the diaper 100 may be attached to one another via suitable fasteners, which include, but are not limited to glue or any suitable adhesive, hook and loop fasteners, ultrasonic welding, other mechanical or chemical fasteners.

Different arrangements of the components depicted in the drawings or described above, as well as components and steps not shown or described are possible. Similarly, some features and sub-combinations are useful and may be employed without reference to other features and sub-combinations. Cases of the invention have been described for illustrative and not restrictive purposes, and alternative cases will become apparent to readers of this patent. Accordingly, the present invention is not limited to the cases described above or depicted in the drawings, and various cases and modifications may be made without departing from the scope of the claims below.

That which is claimed is:

1. A diaper comprising:
   an absorbent core; and
   a chassis surrounding the absorbent core, the chassis comprising:
   a first end and a second end, the first end comprising at least two tabs, wherein:
   each of the at least two tabs comprises a fastening portion, the fastening portion comprising a grip portion and a handle portion;
   each grip portion is configured to removably attach to a portion of the second end;
   each fastening portion comprises at least one cut portion extending through an entire thickness of the fastening portion;
   during disengagement of the fastening portion from the second end, the diaper is configured such that a peeling force resists detachment of the fastening portion from the second end before detachment of the fastening portion reaches a pair of end points of the at least one cut portion; and
   during disengagement of the fastening portion from the second end, the diaper is configured such that a shear force resists detachment of the fastening portion from the second end after the detachment of the fastening portion reaches the pair of end points of the at least one cut portion.

2. The diaper of claim 1, wherein at least one leading portion of the at least one cut portion, a first end point of the at least one cut portion, and a second end point of the at least one cut portion are disposed inside the grip portion.

3. The diaper of claim 2, wherein the at least one cut portion comprises a concave shape and wherein the at least one leading portion is disposed closer to the handle portion than the first and second end points.

4. The diaper of claim 1, wherein the at least one cut portion comprises a portion of a circular arc.

5. The diaper of claim 1, wherein a width of the at least one cut portion is less than a minimum width of the handle portion.

6. The diaper of claim 1, wherein the at least one cut portion comprises at least two V-shaped cut portions.

7. The diaper of claim 1, wherein the at least one cut portion comprises:
   at least one leading portion disposed within the grip portion; and
   two end points disposed outside the grip portion.

8. The diaper of claim 1, wherein the peeling force is applied to pull a portion of the grip portion outside of the at least one cut portion away from the second end.

9. The diaper of claim 1, wherein the shear force is applied to pull an area of the grip portion inside of the at least one cut portion away from the second end.

10. The diaper of claim 1, wherein, after pulling an area inside the at least one cut portion away from the second end, the diaper is configured such that a second peeling force resists detachment of the fastening portion from the second end.

11. An attachment tab for use with a diaper comprising:
    a fastening portion comprising a handle portion disposed at a distal edge of the fastening portion and a grip portion;
    wherein the grip portion is disposed between the handle portion and a proximal edge of the fastening portion;
    wherein the grip portion is configured to removably attach to a second end;

wherein the fastening portion comprises at least one cut portion extending through an entire thickness of the fastening portion;

wherein during disengagement of the fastening portion from the second end, the diaper is configured such that a peeling force resists detachment of the fastening portion from the second end before detachment of the fastening portion reaches a pair of end points of the at least one cut portion; and wherein during disengagement of the fastening portion from the second end, the diaper is configured such that a shear force resists detachment of the fastening portion from the second end after the detachment of the fastening portion reaches the pair of end points of the at least one cut portion.

12. The attachment tab of claim 11, wherein a width of the at least one cut portion is less than a minimum width of the fastening portion.

13. The attachment tab of claim 11, wherein the handle portion and the grip portion each extend across a width of the fastening portion.

14. The attachment tab of claim 11, wherein the at least one cut portion comprises at least one leading portion, a first end point, and a second end point.

15. The attachment tab of claim 14, wherein the first end point and the second end point of the at least one cut portion are disposed inside the grip portion.

16. The attachment tab of claim 14, wherein the at least one cut portion comprises a concave shape and wherein the at least one leading portion is disposed closer to the handle portion than the first and second end points.

17. The attachment tab of claim 16, wherein the at least one cut portion comprises a portion of a circular arc.

18. The attachment tab of claim 11, wherein the grip portion comprises at least one of (i) adhesive, (ii) a plurality of hooks or (iii) a plurality of loops.

19. The attachment tab of claim 11, further comprising:
a second at least one cut portion disposed in the attachment tab adjacent to the proximal edge of the fastening portion; and
a second grip portion on the second end configured to interface with the second at least one cut portion.

* * * * *